United States Patent [19]

Taccone

[11] 3,979,395

[45] Sept. 7, 1976

[54] PROCESS FOR THE PREPARATION OF VINCAMINE AND OTHER INDOLE ALKALOIDS

[75] Inventor: Ida Taccone, Voghera (Pavia), Italy

[73] Assignee: Buskine S.A., Fribourg, Switzerland

[22] Filed: Aug. 6, 1975

[21] Appl. No.: 602,520

[30] Foreign Application Priority Data
Aug. 9, 1974   Switzerland.................. 10940/74

[52] U.S. Cl. .................. 260/293.53; 260/293.55
[51] Int. Cl.² .................................. C07D 471/22
[58] Field of Search .................. 260/293.53

[56] References Cited
UNITED STATES PATENTS

| | | | |
|---|---|---|---|
| 3,454,583 | 7/1969 | Kuehne | 260/294.3 |
| 3,770,724 | 11/1973 | Warnant et al. | 260/239.3 P |
| 3,884,927 | 5/1975 | Martel et al. | 260/293.53 |
| 3,925,392 | 12/1975 | Najer et al. | 260/293.53 |

*Primary Examiner*—G. Thomas Todd
*Attorney, Agent, or Firm*—Haseltine, Lake & Waters

[57] ABSTRACT

The invention relates to the preparation of vincamine and similar indole alkaloids, capable of being easily converted to vincamine, by oxydating a starting alkaloid selected between tabersonine and vincadifformine with oxygen, the reaction mixture being added with an essential amount of an inorganic or organic salt of a metal selected among Cu, Fe and Co.

8 Claims, No Drawings

PROCESS FOR THE PREPARATION OF VINCAMINE AND OTHER INDOLE ALKALOIDS

The present invention relates to the preparation of vincamine and similar alkaloids, adapted to be converted into this substance.

The vincamine, having the formula

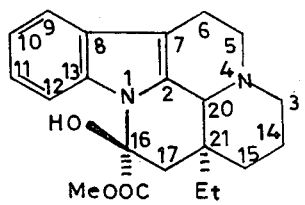

is an alkaloid which was isolated from Vinca minor, from which it is still commonly extracted as well as from other plants.

This group of alkaloids, particularly the vincamine, possesses interesting pharmacological properties, especially of hypotensive and sedative type, which make it suitable for an efficacious treatment of diseases of the circulatory system and of the central nervous system.

There have been proposed in the past several methods of synthesis; either partial or total, of the vincamine as well as of other alkaloids of the same family.

By total synthesis the preparation of the substance starting from compounds of simple structure is meant: as an example, the fundamental synthesis of Kuhne (U.S. Pat. No. 3,454,583 can be cited, according to which a lactam is prepared from tryptamine and 4-ethyl-formyl-dimethyl-pimelate, the lactam being then converted to the thiolactam by reaction with phosphorus pentasulfide, and to the aminoester by desulfuration; the aminoester is then converted to dl-vincamine by oxidation and acid hydrolysis. The other methods of total synthesis known to date are based on this synthesis (French Patent Nos. 2,081,593, 2,104,959, 2,190,113, 2,143,657, and 2,178,024, although several variations, either as regards the reagents taking part in the reactions, or as regards the conditions of the same reactions, are contemplated.

The methods which can be considered as partial syntheses are, on the contrary, based on the conversion of other indole alkaloids.

By mentioning only the most important among these methods, the following can be cited:

a. The French Patent No. 2,108,947 describes a reductive trans transposition, in the presence of zinc, of the 1-tabersonine having the formula:

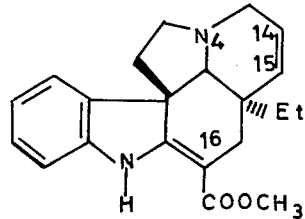

to the aminoester; the subsequent oxidation with mercuric acetate to the immonium salt; the reduction with an alkaline borohydride to the d-aminoester and the final conversion to d-vincamine by oxidation and hydrolysis, provided that, in any step of the process, the double bond (14–15 of the tabersonine is reduced.

b. In the Belgian Patent Nos. 761,628 and 763,730 the catalytic hydrogenation of the tabersonine to vincadifformine or 14-15-dihydro-tabersonine having the formula:

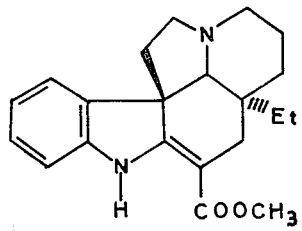

is effected, the latter being then oxidated with peracids and in several stages to N-oxy-16-hydroxy-vincadifformine. This compound, through reduction and transposition in acid medium is converted to the vincamine which is obtained as a mixture with epi-16-vincamine and apo-vincamine. The vincamine is isolated from this mixture by chromatography and subsequent crystallization.

According to a modification of this process, the vincamine is prepared from the 16-hydroxy-derivative of the vincadifformine as obtained by catalytic oxidation of vincadifformine or tabersonine, $PtO_2$ being used as the catalyst for the preparation in heterogeneous phase of the same 16-hydroxy-vincadifformine; organic peroxides or oxides or salts or oxides of heavy metals are used in the preparation of other oxidation derivatives.

c. The preparation of enantiomers of the vincamine by a method analogous to that described under under (b) is disclosed in the Belgian Patent 765,795.

d. A method for the so-called epimerization, namely for the conversion of the 16-epivincamine into vincamine is described in the French Patent No. 2,123,521.

The main problems and drawbacks of these methods according to the prior art can be summarized as follows:

1. the extraction methods, besides being dependent on the availability of the vegetal material, have relevantly low yields of vincamine and involve rather complicate steps for the isolation and the purification of the vincamine from the whole extract;
2. the methods of total synthesis need of a number of steps which, apart from their intrinsic problems, are surely causing the yields to be strongly lowered;
3. the methods of partial synthesis are still involving three or more steps, (if the isolation of the intermediate reaction product is taken into account).

The main purpose of the present invention is that of providing a method for the partial synthesis of the vincamine which, starting from easily available compounds, namely the tabersonine and the vincadifformine, as already above identified, permits the desired product to be obtained through a minor number of steps and with industrially advantageous yields.

It is now to be printed out that the tabersonine and the vincadifformine are very widespread indole alkaloids, which are present in several parts of the plants and mostly in the seeds of several botanic species of the Apocinaceae family:

*Amsonia Tabernaemontana*
*Amsonia sps*

*Catharanthus sps*
*Conopharingia sps*
*Crioceras sps*
*Schizozygia coffaeoides*
*Tabermaemontana sps*
*Vinca sps*
*Voacanga obtusa*
*Voacanga africana*
*Voacanga lutescenes*
*Voacanga thouarsii*
*Voacanga chalotiana*
*Voacanga schweifurtii*
*Voacanga sps*
*Rhazya stricta.*

It has been found that the above purpose is achieved according to the present invention by a method for the preparation of vincamine and similar alkaloids which, starting from the tabersonine and/or the vincadifformine, permits the required conversion to be obtained in but one step and in homogeneous phase, and is characterized in that the starting compound, as a solution in a polar solvent, is added, in the ratio of 1:1 to 1:5 of the weight of the starting alkaloid, with an inorganic or organic salt, soluble in the reaction medium of a metal selected among Cu, Fe and Co, said metal being at the highest valence state, the reaction being carried out in the presence of oxygen, at a temperature of between 10° and 50°C and for 5 to 15 days, preferably in acid environment.

The reaction of the method according to the present invention can be schematically written as follows:

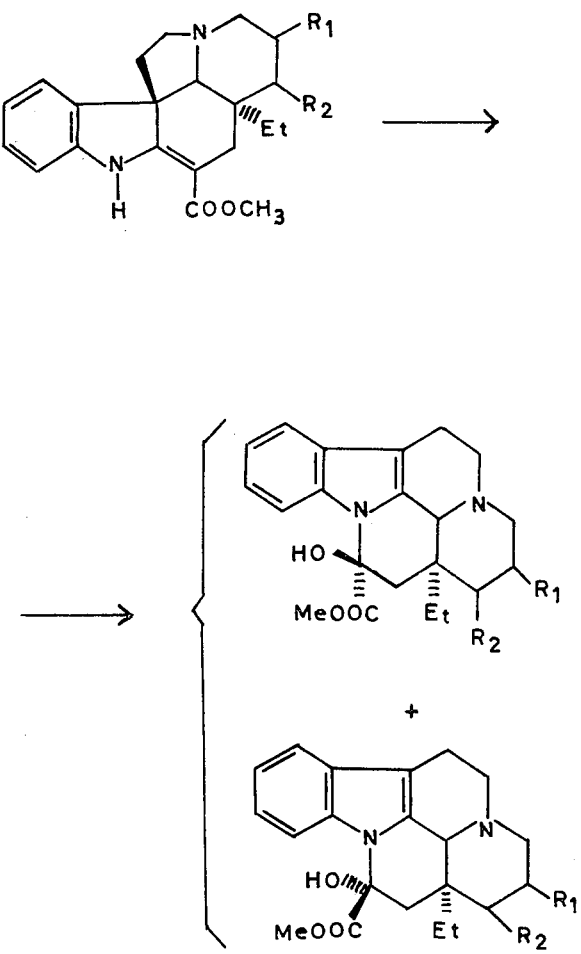

in which $R_1$ and $R_2$ are respectively representing hydrogen or, if taken together a double bond.

From the preceding scheme it will be clear that, when $R_1=R_2=H$, the starting compound is the vincadifformine and a mixture of vincamine and epivincamine is obtained when, on the contrary $R_1$ and $R_2$ taken together represent a double bond, the starting compound is the tabersonine and the resulting compounds are the $\Delta^{14}$-vincamine and the $\Delta^{14}$-epivincamine, the catalytic reduction of which to the corresponding above said compounds is readily and easily carried out.

As already mentioned, the reaction according to the present invention is effected with the intervention of a salt of a metal selected among $Cu^{++}$, $Fe^{+++}$, $Co^{++}$, with an organic or inorganic acid. Particularly useful for the present invention are the copper sulphate $CuSO_4$, the ferric chloride $FeCl_3$, the cobalt stearate.

With respect to the reaction solvent, it is preferably selected in the group comprising alcohols, hydroalcoholic mixtures, acrylonitrile, dimethylformamide, and hexamethylenphosphortriamide.

Lastly, in order to provide the reaction acid environment, even if the use, as the starting compound, of the hydrochloride of tabersonine or of vincadifformine is sufficient, more advantageous appears to be the addition of an acid, preferably an aqueous solution of an inorganic acid. Even if the reaction mechanism has not yet been clarified, it seems probable that the reaction conditions are permitting the formation, in the reaction mixture, of the 16-hydroxy-derivative, without the oxidizing attack at the nitrogen atom in the position 4, namely without the formation of the N-oxy-16-hydroxy compound, through which essentially all the methods of partial synthesis known to date are passing. Such a 16-hydroxy-derivative becomes directly converted, without being isolated and as soon as it is formed, to the final compounds above referred to.

Thus the reaction can take place in only one step and with satisfactory yields of vincamine or $\Delta^{14}$-vincamine. Unknown and surprising is the effect of the metal salt, taking it into account that it is added in an amount widely higher than those of normal use for the catalysts.

The reaction can be effected under stirring or keeping the reaction mixture under an air stream or, preferably, of oxygen for a time variable from 5 to 15 days, at a temperature of between 10° and 50°C.

At the end of the reaction, aqueous ammonia is added until the neutrality is attained and then the mixture is extracted with chloroform. The chloroform residue is subjected to chromatography on silica gel, by eluating with chloroform and increasing amounts of MeOH.

The following examples illustrate the invention, without having to be construed as a limitation thereof.

EXAMPLE 1

11.4 grams (about $3.10^{-2}$ mole) of (−)-vincadifformine hydrochloride are dissolved under stirring at 50°C in 240 mls of ethyl alcohol. To the resulting solution, a mixture of 240 mls of $H_2O$, 60 mls of 10% HCl and 2.5 g. of $CuSO_4.5H_2O$ is added and maintained under an $O_2$ stream at 50°C during about 8 days. The conversion to vincamine and epivincamine is monitored by thin layer chromatography (TLC), using 2.4% NaOH silica gel, as the adsorbent, and a mixture of chloroform-methanol (96:4) as the eluant. The spots are detected by spraying the plate with the cerium-ammonium sulphate (C.A.S.)

reagent (Stahl reag. No. 34), and revealed under the Wood light and under normal light.

More particularly, the vincadifformine is identified by an intense blue spot under visible light, whereas the vincamine and the epivincamine are identified by more polar and highly fluorescent spots at 366 nm. The reaction mixture is made alkaline at pH 8 by the cold addition of about 300 mls of a solution of 10% $NH_4OH$, and is then extracted three times with portions each of 500 mls of $CHCl_3$. The organic phases are separated, combined, washed with water and dried over anhydrous $Na_2SO_4$. The solution is then filtered and evaporated at 40°C under reduced pressure until a dry residue is obtained. About 9 g. of raw residue are obtained, which are taken up with 20 mls of a mixture of acetone, -methylen chloride, -methanol in the ratio 5:4.9:0.1, and subjected to column chromatography, silica gel being used as the absorbent and the same solvent mixture as the eluant.

The first 3000 mls of the eluate are discarded, whereas the subsequent about 1500 mls give, after evaporation of the solvent, (−)-vincadifformine (about 0.9 g. = 10%) is obtained, m.p. 96°C from methanol, $M^+ = 338$.

The recovered vincadifformine is recicled to the reaction. Further 5000 mls of the eluate are discarded and, at the end, two series of fractions are obtained, the first giving, after evaporation of the solvent, (+)vincamine (2.7 g. = 30%), m.p. 230°–232°C, from MeOH; $[\gamma]_D^{20} = + 41$ ($CHCl_3$, c=1), $M^+ = 354$. I.R. (nujol) bands at: 1756, 1074, 747, 727 ($cm^{-1}$), and epivincamine (1.35 g. = 15%), m.p. 190°–192°C from acetone, $M^+ = 354$; $[\gamma]_D^{20} = - 39°$ ($CHCl_3$, c = 1).

EXAMPLE 2

6.70 grams ($2.10^{-2}$mole) of tabersonine, as the base, are dissolved in 200 mls of ethanol. The solution is then added with 4 mls of 10% HCl and 5 g. of $CuSO_4$ $5H_2O$ previously dissolved in a mixture of 160 mls of $H_2O$ and 40 mls of 10% HCl, and then maintained under an $O_2$ stream in a thermostatized bath at 50°C during 10–12 days.

The conversion of the tabersonine to $\Delta^{14}$-vincamine and $\Delta^{14}$-epivincamine is monitored by TLC using silica gel as the absorbent and a mixture of acetone-methylen chloride-methanol (20:80:0.5) as the eluant. The spots are detected by spraying the plate with the C.A.S. and revealed by U.V. light ($\lambda = 366$ nm.). At the end of the reaction, the solution is made alkaline by the cold addition of 10% $NH_4OH$ and extracted several times with $CH_2Cl_2$. The organic phases are washed until neutral with $H_2O$, dried over anhydrous $Na_2SO_4$, filtered and then concentrated at >40°C under reduced pressure until a dry residue is obtained. 5.6 g. of raw product are obtained, which are taken up with 15 mls of a mixture of acetone-methylen chloride (2:8) and subjected to chromatography on a silica gel column (250 g.). The acetone-$CH_2Cl_2$ eluate comprises a first series of fraction containing $\Delta^{14}$-vincamine (20%), m.p. 218°C from methanol $[\gamma]_D^{20} = +115°$ ($CHCl_3$, c=1); $M^+ = 352$ U.V. (MeOH)$\lambda$=223(4, 50), 271(3, 95), 278(3, 90), 288(3, 70) $\lambda$=(nm)(log$\epsilon$)
whereas the eluate $CHCl_3$—MeOH (95:5) gives a second series of fractions containing the $\Delta^{14}$-16-epivincamine (10%), m.p. 184°C from acetone $[\gamma]_D^{20}=+31°$ ($CHCl_3$, c = 1); $M^+=352$; U.V. (EtOH)$\lambda_{nm(log\epsilon)}=$ 224(4, 30), 270(3, 85), 280(3, 79), 291(3, 60).

EXAMPLE 3

3.38 grams of vincadifformine ($10^{-2}$mole), as the free base, are treated with 80 mls of water, 20 mls of 10% HCl, 100 mls of ethanol and 2.71 g. of $FeCl_3$ at 50°C in a thermostatized bath under $O_2$ atmosphere. The conversion of the vincadifformine to vincamine and 16-epivincamine is monitored by TLC under the same conditions of the Example 1.

After about 10 days of reaction, the reaction mixture is made alkaline by adding 10% $NH_4OH$ and extracted several times with $CHCl_3$.

The organic solutions are separated, washed with $H_2O$, dried over $Na_2SO_4$, filtered and concentrated to a dry residue, at 40°C under reduced pressure. 2.5 g. of residue are obtained, which are taken up with 5 mls of $CHCl_3$ and subjected to chromatography on a silica gel column under the conditions of the Example 1. The yield of the vincamine recovered from the concentration of the useful fractions is 0.8 grams (30%).

EXAMPLE 4

6.60 g. of vincadifformine ($2.10^{-2}$mole) are dissolved in 500 mls of ethanol. To the solution 10 mls of $H_2O$, 50 mls of dimethylformamide (DMF) and 1.5 g. of $CuSO_4.5H_2O$ are added. The mixture is maintained at room temperature by bubbling $O_2$ thereinto during about 8 days.

The conversion to vincamine and 16-epivincamine is monitored by TLC, using the eluant system of the Example 1.

The solution is then concentrated to a small volume under reduced pressure, then added with 300 mls of $H_2O$, adjusted to pH 9 by adding 10% $NH_4OH$ and extracted with $CHCl_3$. The combined organic solutions are washed with water, dried over $Na_2SO_4$, filtered and concentrated to dryness under high vacuum.

About 3 g. of residue are obtained, which are taken up with 20 mls of $CHCl_3$ and subjected to column chromatography under the conditions of the Example 1, and the yields of vincamine and 16-epivincamine are 8.4% and 12%, respectively.

EXAMPLE 5

10 g. of tabersonine HCl are dissolved in 100 mls of methyl alcohol. The resulting solution is added with 1 g. of cobalt stearate and kept standing in air for 15 days. The conversion is monitored by TLC on silica gel 2.5 NaOH as the absorbent and a mixture of chloroform-methanol (96:4) as the eluant. Upon disappearance of the tabersonine, the solution is made neutral with cold addition of 5% $NH_4OH$ diluted with 100 mls of $H_2O$ and extracted three times with 100 mls portions of chloroform.

The combined extracts are made anhydrous over $K_2CO_3$ and the chloroform solution is concentrated under reduced pressure at 30°–40°C until a constant residue is obtained. 9 g. of residue are obtained, which are taken up with 20 mls of $CHCl_3$ and fed to a chromatographic column equilibrated with 250 g of silica gel.

The chloroformic eluate comprises a first series of* fractions containing $\Delta^{14}$-vincamine (2 g.), m.p. 218°C from methanol; $[\gamma]_D^{20}=+115°$ ($CHCl_3$; c=1); $M^+ = 352$; U.V. = MeOH$\lambda$ = 223 (4, 50), 271(3, 95), 278(3, 90), 288(3, 70). The eluate chloroform-MeOH (95:5) gives a second series of fractions containing the $\Delta^{14}$-epivincamine (3 g.), m.p. 184°C from acetone:

$[\gamma]_D^{20} = +31°$ (CHCl$_3$, c=1); M$^+$ = 352; U.V. = EtOH$\lambda$ = 224(4, 30), 270(3, 79), 280(3, 79), 291(3, 60).

EXAMPLE 6

10 g. of vincadifformine HCl are dissolved in 100 mls of methanol. The resulting solution is added with 1 g. of cobalt stearate and maintained on standing for 15 days. The conversion is monitored by TLC, using 2.5% NaOH silica gel as the adsorbent and a mixture of CHCl$_3$-MeOH (96:4) as the eluant.

Upon disappearance of the vincadifformine, the solution is neutralized with cold 5% NH$_4$OH, diluted with 100 mls of water and extracted three times with 100 mls portions of CHCl$_3$. The combined extracts are made anhydrous over K$_2$CO$_3$ and the chloroformic solution is concentrated under reduced pressure at 30° – 40°C until a constant residue is obtained.

7.5 – 7.8 grams of residue are obtained, which are taken up with 20 – 25 mls of CHCl$_3$ and charged in a chromatographic column equilibrated with 250 g. of silica gel. The chloroformic eluate comprises a first series of fractions containing vincamine (1.9 g.), m.p. 230° – 232°C from MeOH $[\gamma]_D^{20} = +41°$ (CHCl$_3$, c=1), M$^+$=354, whereas the eluate from CHCl$_3$—MeOH (93:7) gives a second series of fractions containing the 16-epivincamine (about 2.5 g.), m.p. 190° – 192°C from acetone, $[\gamma]_D^{20} - 39°$ (CHCl$_3$, c=1), M$^+$ 354.

What I claim is:

1. A method for the preparation of vincamine and similar indole alkaloids, starting from tabersonine or vincadifformine, characterized in that the starting compound, as a solution in a polar solvent, is added, in the ratio of 1:1 to 1:5 by weight of the starting alkaloid, with an inorganic or organic salt, soluble in the reaction medium, of a metal selected among Cu, Fe and Co, said metal being at the highest valence state thereof, the reaction being carried out in the presence of oxygen, at a temperature of between 10° and 50°C and for a time of between 5 and 15 days.

2. A method according to claim 1, characterized in that the reaction is carried out in acid environment.

3. A method according to claim 1, characterized in that said metal salt is cupric sulphate.

4. A method according to claim 1, characterized in that said metal salt is ferric chloride.

5. A method according to claim 1, characterized in that said metal salt is a salt of cobalt of a monocarboxylic acid.

6. A method according to claim 2, characterized in that said acid environment is obtained by using the hydrochloride of the starting alkaloid.

7. A method according to claim 2, characterized in that said acid environment is obtained by adding an inorganic acid in aqueous solution to the reaction mixture.

8. A method according to claim 1, characterized in that said polar solvent is selected in the group consisting of alcohols, hydro-alcoholic mixtures, acrylonitrile, dimethyl-formamide and hexamethylenphosphortriamide.

* * * * *